United States Patent [19]

Otsuka et al.

[11] 4,173,615
[45] Nov. 6, 1979

[54] CHEMICAL APPARATUS FOR CORROSIVE MATERIALS

[75] Inventors: Eiji Otsuka, Yokohama; Shigeru Inoue; Tetsuo Kimura, both of Kamakura; Toshinori Takae, Tokyo; Morio Tsuji; Toshiki Kato, both of Osaka, all of Japan

[73] Assignee: Mitsui Toatsu Chemicals, Incorporated, Tokyo, Japan

[21] Appl. No.: 809,673

[22] Filed: Jun. 24, 1977

Related U.S. Application Data

[62] Division of Ser. No. 591,285, Jun. 30, 1975.

[30] Foreign Application Priority Data

Jul. 8, 1974 [JP] Japan .................................. 49/77374

[51] Int. Cl.² ............................. B01J 1/00; B01J 1/20
[52] U.S. Cl. .................................... 422/197; 165/174; 422/201
[58] Field of Search ................. 23/284, 285, 283, 289, 23/288 M; 165/174, 134; 422/148, 201, 197

[56] References Cited

U.S. PATENT DOCUMENTS

| 452,273 | 5/1891 | Kaiser | 165/174 |
| 3,482,947 | 12/1969 | Jacobson et al. | 23/285 |
| 3,933,434 | 1/1976 | Matovich | 23/252 R |

Primary Examiner—Arnold Turk

[57] ABSTRACT

A reaction apparatus for corrosive material includes a heat exchanger that is coupled to a header. A first inlet is provided for fluid raw material and a second inlet is provided for introducing a non-corrosive material. There is also an outlet for reaction products. A tube baffle is positioned across the interior of the heat exchanger in order to define an inner space therein and an inner member which substantially conforms to the configuration of the inner space is positioned therein in closely spaced relationship with the inside surface of the header. A first plurality of tubes are attached to opening formed in the baffle and a second plurality of tubes are attached to the inner member and are positioned correspondingly to the first tubes in spaced relation thereto and in fluid communication therewith.

2 Claims, 4 Drawing Figures

CHEMICAL APPARATUS FOR CORROSIVE MATERIALS

This is a division of application Ser. No. 591,285 filed June 30, 1975.

FIELD OF THE INVENTION

This invention relates to chemical processes in general wherein the reactants when admixed, form a corrosive environment which is harmful to the reactor and wherein a method has been devised to prevent such corrosion of the reactor. The invention also relates to an apparatus suitable to carry out such method. Typical applications of the method of the invention are, for example, in the process for making isopropyl alcohol from propylene and $H_2SO_4$, or in the manufacture of hydrochloric acid from HCL and water, or in the synthesis of urea.

THE PRIOR ART

In the synthesis of urea by reaction of ammonia and carbon dioxide under urea synthesis pressures and temperatures in an autoclave, for example, the process' most serious difficulty is the occurrence of a severe local corrosion of the autoclave. While a number of proposals have been made to overcome this difficulty, such as for example, by selecting special anti-corrosive materials and passivating them with oxygen in the autoclave, no satisfactory result has yet been achieved for reactors having a built-in heat exchanger which is commonly used for recovering the heat of reaction generated through the exchanger under urea synthesis conditions.

BRIEF SUMMARY OF THE INVENTION

An object of the present invention is therefore to provide a method for carrying out a chemical process during which heat exchange is performed without giving rise to corrosive conditions in the reactor used in the process.

Another object of the present invention is to provide a chemical apparatus for carrying out the method of preventing corrosion in the reactor.

A further and particular object of the present invention is to provide a method for synthetizing urea and an apparatus therefor, whereby the apparatus is prevented from being corroded, while the heat of reaction generated during the process is recovered.

Briefly stated, the present invention resides in an improvement in chemical process and apparatus therefor whereby a plurality of reactants including at least one non-corrosive reactant are reacted in a reaction zone to obtain a corrosive reaction mixture, while concurrently indirectly exchanging heat. The improvement according to the present invention resides in providing a partition or inner member closely spaced from the surface of said reaction zone which is exposed to corrosive environment and flowing a non-corrosive reactant in the spacing between the partition and the said surface in order to prevent the surface from being corroded. The reaction zone, or mixing zone, is located in the header portion of the heat exchanger.

The apparatus of the present invention is actually an improvement in a reactor having an inlet for the reactants at one end and an outlet for the reaction products at another end, an inlet for introducing a non-corrosive fluid and a multi-tube heat exchanger. The improvement provides an inner member which is positioned within the header of the exchanger or of the reactor, with walls closely spaced therefrom, and conformed to the configuration of the inner space defined by the inner surface of the mixing zone of the reactor and the tube sheet or baffle of said multitubular heat exchanger disposed across the interior of the reactor. Further provided is a plurality of smaller tubes connected to said inner member and in fluid communication with the tubes of the heat exchanger.

The reactor with the improvement afforded by the present invention can be of any conventional type, namely a vertical, horizontal or inclined reactor.

The present invention will be described hereinafter in greater detail using as illustrative example the synthesis process of urea from ammonia and carbon dioxide, although the present invention is not limited to merely the urea synthesis, but is applicable to many other equivalent chemical processes. For example, the invention is applicable to the synthesis of iso-propyl alcohol from propylene and sulfuric acid. The same apparatus used for urea synthesis and described hereinafter, can be used, in which case, however, a propylene flow is maintained in the spacing between the header of the exchanger and the inner member contained therein. Another application resides in the preparation of hydrochloric acid from hydrogen chloride and water; again, the same apparatus can be used, in which case a water flow is maintained in the said spacing.

THE DRAWINGS

For a better understanding of the invention, a few embodiments thereof will be described more fully hereinbelow with reference to the accompanying drawings, in which.

Taking the synthesis of urea as an illustrative example, ammonia and carbon dioxide (and ammonium carbamate solution, if necessary) are fed into a mixing zone located in the upper part of the inner member through an inlet positioned at one extremity of the header. From the mixing zone, the reactants flow down along a plurality of tubes connected with the inner member. If desired, the reactants may be mixed prior to being introduced into the mixing zone. Liquid ammonia is supplied at one end of the header and is caused to flow down through the spacing defined by the inside surface of the header and the outside surface of the inner member, and then passes between the outside of the inner member and the header to be ultimately fed into and run through the clearances between the tubes of the heat exchanger and the tubes integrally connected with the inner member. Since the free ends of these latter tubes open into the exchanger tubes or are communicating therewith through small clearances, the liquid ammonia is subsequently mixed with the reactants discharged from the tubes of the inner member. The contact effected by the inside surface of the header and by the tube baffle with the flow of liquid ammonia is sufficient to inhibit corrosion.

Figure 1:
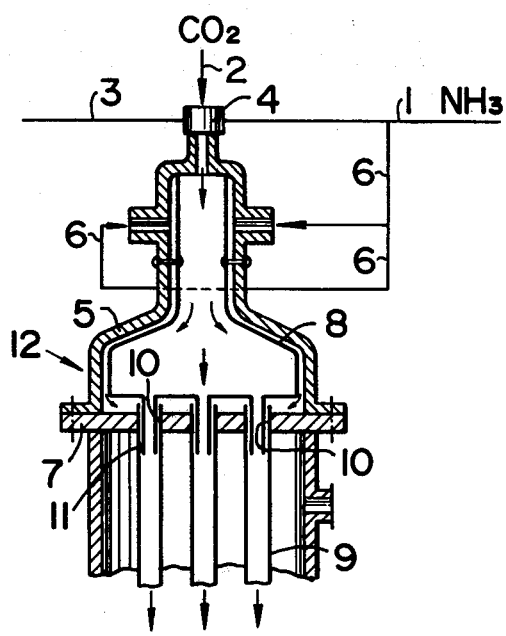
FIG. 1 is a schematic cross-sectional, partial elevational view of a heat exchanger of a reactor, containing the improvement in accordance with one embodiment of the invention.

Referring now specifically to FIG. 1, there is shown in cross-section the upper part of a heat exchanger containing an embodiment of the invention, which may be used in the urea synthesis. The exchanger is constructed so that, prior to feeding into the synthesis zone, liquid ammonia, carbon dioxide and an aqueous ammonium carbamate solution (under urea synthesis pressure) are passed inside the tubes of the multitubular head exchanger from which the heat generated during the formation of ammonium carbamate from carbon dioxide and ammonia is recovered as steam on the shell side of the heat exchanger.

Liquid ammonia line 1, carbon dioxide line 2 and aqueous ammonium carbamate solution line 3 are connected together in an inlet zone 4 for admission of the fluid mixture into a header 5. After mixing, the carbon dioxide is not entirely converted into liquid carbamate under the normal pressure used for urea synthesis, but there remains a substantial proportion of carbon dioxide gas together with an excess amount of ammonia. The resulting gas-liquid mixture causes severe corrosion of the tube baffle 7, in particular where the tubes 9 of the exchanger are welded to the tube baffle 7. Branch lines 6 from line 1 introduce liquid ammonia into the header 5 through its top for controlling the corrosion thereof. Horizontal tube baffle 7 extends across the entire header 5 to define a space therewith. An inner member 8 made of a corrosion-resistant material such as an 18 Cr-8 Ni stainless steel is inserted and positioned in the space thus defined; fastening means such as bolts or the like secure it to the header 5. Inner member 8 is open at its top for admission of ammonia, carbon dioxide and ammonium carbamate solution thereinto. Liquid ammonia flows down in the clearance or spacing kept between the inner member 8 and the inside surface wall of the header 5 in an amount sufficient to maintain an uninterrupted flow. The liquid ammonia accumulates on the tube baffle 7, and then flows down the plurality of tubes 9 through a plurality of openings 10 formed in the tube baffle 7, or more specifically through the gaps formed between these tubes 9 and tubes 11 which latter are integrally connected with the bottom surface of the member 8. The gas-liquid mixture comprising ammonia, carbon dioxide and ammonium carbamate solution is discharged from the openings existing in the lower end of the tubes 11, whereby it is mixed with the flow of liquid ammonia which is delivered down the gaps between tubes 9 and tubes 11. The distance through which the tubes 11 extend into tubes 9 is predeterminedly chosen to provide an adequate protection against corrosion of the header walls while avoiding a loss in the heat transfer effect. Alternatively the extremities of tubes 11 may open spacedly over the top ends of the exchanger tubes 9. As mentioned previously, the heat generated by the reaction and removed by the exchanger is utilized to produce steam.

Figure 2:
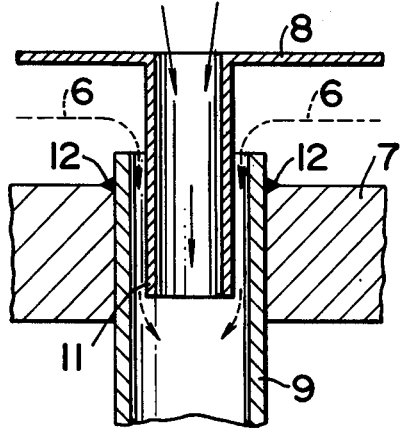
FIG. 2 is a fragmentary enlarged sectional view of the exchanger shown in FIG. 1.

FIG. 2 is a fragmentary enlarged view further illustrating the relationship between tube baffle 7, and tubes 9 and tubes 11 in the embodiment shown in FIG. 1. Tubes 9 are joined such as at welds 12 to the wall of the openings 10 in the baffle 7 so as to extend downwardly therefrom, and tubes 11 are individually inserted into the respective tubes 9. Tubes 11 may be suitably thinner in wall thickness and are open at their lower end. The solid arrows shown in FIG. 2 indicate the main mixed flow, while the broken arrows indicate the flow of the liquid ammonia which passes through tubes 9 and the smaller tubes 11. Both flows merge together below the lower extremity of the tubes 11.

Figure 3:
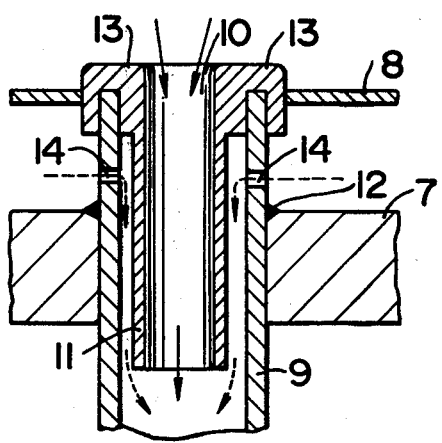
FIG. 3 is a fragmentary enlarged sectional view of another embodiment of heat exchanger of the invention.

FIG. 3 shows a modification similar to the previous embodiment except that tubes 11 have fitting means or caps 13 which bear against the openings formed in the bottom of the inner member 8 and into which the tops of the tubes 9 are fit so as to have them protrude a little into the member 8. In addition, tubes 9 are formed with side apertures 14 for the passage of liquid ammonia as indicated by the arrows and broken lines. This arrangement is advantageous in that the inner member 8 and the tubes 11 can be manufactured separately from each other.

Figure 4:
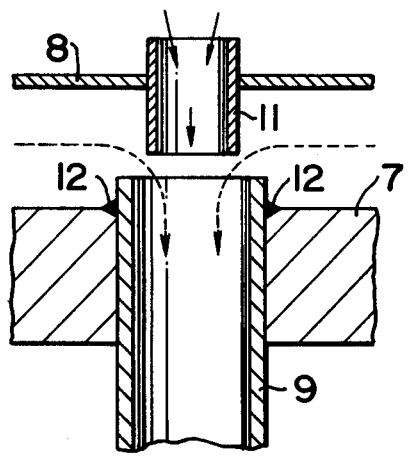
FIG. 4 is a fragmentary enlarged sectional view of still another embodiment of the exchanger of the invention.

In a further embodiment of the invention, tubes 11 are connected with the bottom of the inner member 8 as clearly shown in FIG. 4 and are positioned over the openings of tubes 9 (joined with baffle 7) leaving a clearance between the two tubes 11 and 9. Through the clearance liquid ammonia flows into tubes 9.

While in the above description, both flows of the gas-liquid mixture and of the liquid ammonia are directed downwardly, these flows may both be directed upwardly with equally satisfactory effect. Furthermore, although the above described embodiments of the apparatus are of the so-called vertical type, the reactor may also be disposed in the horizontal or in an inclined position. The gas-liquid mixed flow in the inner member 8 or the liquid ammonia flowing between the header of the heat exchanger and the inside member 8 can be introduced into the tubes of the heat exchanger provided in a reactor of horizontal or inclined type in the same way as in one of the vertical type, because of the pressure exerted by the continuously introduced non-corrosive single flow.

The invention has been described hereabove as utilizing the heat exchanger specifically for removal of the heat of reaction generated; however, it will be appreciated that it can equally be utilized for other purposes: in the case of urea synthesis for example, when unreacted ammonium carbamate contained in the melt is heat-stripped with carbon dioxide by introducing it into the shell side of the heat exchanger to decompose into ammonia and carbon dioxide, the ammonia can be replaced by a small quantity of carbon dioxide.

From the foregoing description, it will be understood that the invention provides an improved structure for reactors having a built-in heat exchanger, which prevents corrosion of the inside of the wall of the header of the exchanger and which also facilitates replacement thereof in the event this is needed.

What is claimed is:

1. Reaction apparatus of the vertical type comprising: a vertically disposed heat exchanger having upper and lower ends; a header coupled to the upper end of said heat exchanger; a tube baffle having an upper surface disposed across the interior of said heat exchanger in a substantially horizontal plane to define an inner space with said header; an inner member made of a corrosion-resistant material positioned in said inner space forming a chamber closely spaced from the inside surface of said header and conforming to the configuration of said inner space; a first inlet in said header for introducing corrosive fluid raw materials into said inner member; a second inlet for introducing a non-corrosive fluid, said second second inlet being connected to said header to supply the non-corrosive fluid between said header and said inner member; an outlet for reaction products; a plurality of openings formed through said tube baffle; a first plurality of vertical tubes attached to said tube baffle and extending through said openings, the upper end of said first plurality of tubes extending above the upper surface of said tube baffle whereby the upper end of said first plurality of tubes are well as the interior surface thereof are protected from contact with the corrosive fluid that might accumulate on the upper surface of said tube baffle; and a second plurality of vertical tubes attached to and extending downwardly from said inner member and positioned coaxially with respect to said first plurality of vertical tubes, said second plurality of vertical tubes being spaced radially inwardly from said first plurality of vertical tubes and in fluid communication therewith for defining an annular space having a vertical plane located between the interior surface of said first plurality of vertical tubes and the exterior surface of said second plurality of vertical tubes, said annular space being located to receive the flow of non-corrosive fluid from said second inlet whereby the corrosive fluid from said first inlet and the non-corrosive fluid from said second inlet are combined within said first plurality of vertical tubes below the lower end of said second plurality of vertical tubes.

2. The reaction apparatus as claimed in claim 1 wherein the first and second plurality of vertical tubes are axially spaced from each other.

* * * * *